United States Patent
Janik

(10) Patent No.: US 6,786,099 B2
(45) Date of Patent: Sep. 7, 2004

(54) SURFACE PHOTO-ACOUSTIC FILM MEASUREMENT DEVICE AND TECHNIQUE

(75) Inventor: Gary Janik, Palo Alto, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/077,373

(22) Filed: Feb. 14, 2002

(65) Prior Publication Data

US 2003/0150272 A1 Aug. 14, 2003

(51) Int. Cl.[7] .......................... G01N 9/18; G01B 11/28
(52) U.S. Cl. ...................... 73/655; 73/657; 356/485
(58) Field of Search ........................ 73/655, 657, 658, 73/661, 597, 598, 602; 356/485, 630, 448, 357

(56) References Cited

U.S. PATENT DOCUMENTS

| | | | |
|---|---|---|---|
| 4,710,030 A | 12/1987 | Tauc et al. .................. 356/432 |
| 4,939,738 A * | 7/1990 | Opower ....................... 372/95 |
| 5,033,304 A * | 7/1991 | Rosen ......................... 372/38 |
| 5,408,882 A * | 4/1995 | McKinley et al. ............. 73/597 |
| 5,546,811 A | 8/1996 | Rogers et al. ................ 73/800 |
| 5,633,711 A | 5/1997 | Nelson et al. ............... 356/318 |
| 5,748,317 A | 5/1998 | Maris et al. ................ 356/357 |
| 5,812,261 A | 9/1998 | Nelson et al. ............... 356/318 |
| 5,959,735 A | 9/1999 | Maris et al. ................ 356/381 |
| 5,982,482 A | 11/1999 | Nelson et al. ............ 356/237.1 |
| 6,069,703 A | 5/2000 | Banet et al. ................ 356/432 |
| 6,081,330 A | 6/2000 | Nelson et al. ............... 356/318 |
| 6,122,064 A | 9/2000 | Banet et al. ................ 356/381 |
| 6,188,478 B1 | 2/2001 | Fuchs et al. ................ 356/381 |
| 6,195,198 B1 * | 2/2001 | Hatori ....................... 359/332 |
| 6,445,457 B1 * | 9/2002 | Early ........................ 356/630 |
| 6,496,268 B1 * | 12/2002 | McKie et al. ............... 356/503 |

\* cited by examiner

Primary Examiner—Hezron Williams
Assistant Examiner—Jacques M. Saint-Surin
(74) Attorney, Agent, or Firm—Parsons Hsue & de Runtz LLP

(57) ABSTRACT

A method for determining the thickness and other properties of a metal layer comprising producing an acoustic wave at a first frequency in the metal layer with a first laser beam, measuring the angle of diffraction of a second laser beam from the acoustic wave, and calculating the wavelength of the acoustic wave and thickness of the metal layer from the angle of diffraction.

40 Claims, 2 Drawing Sheets

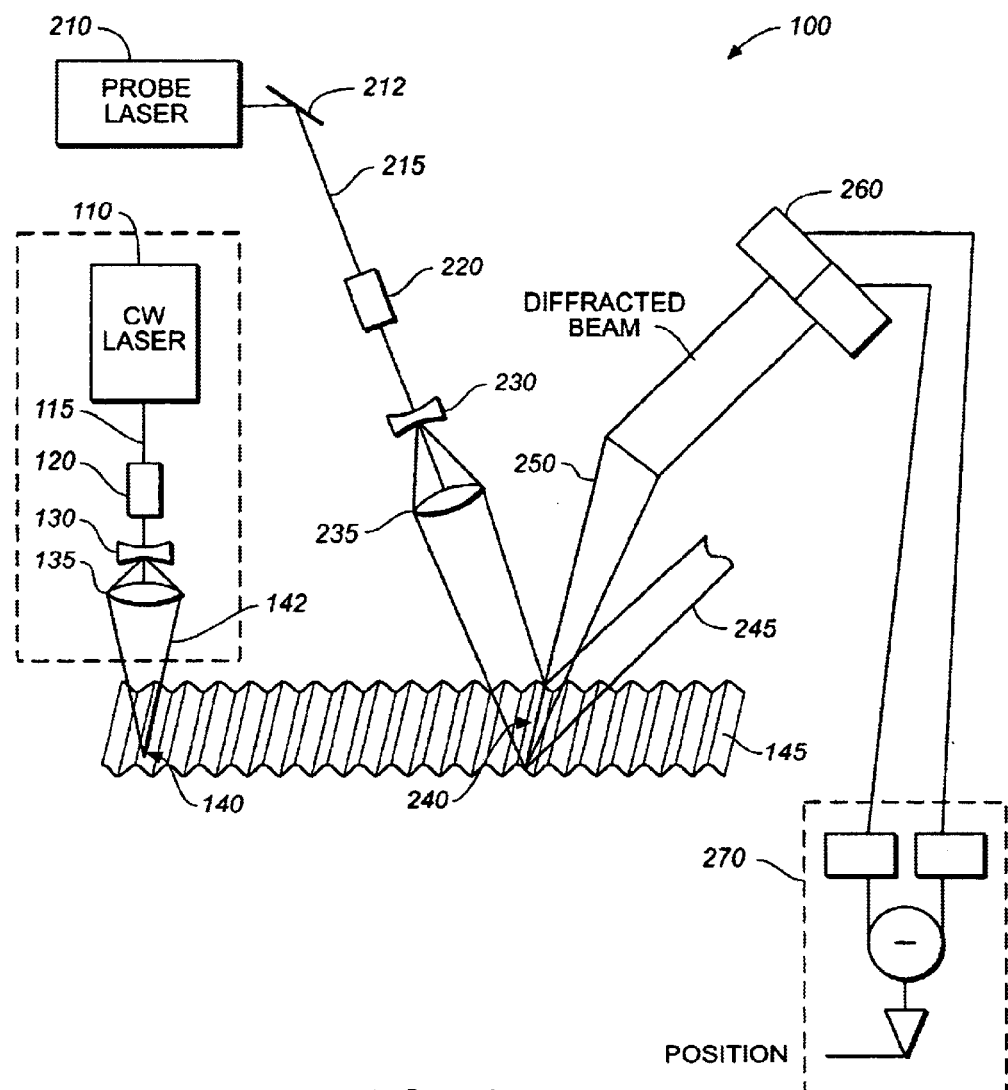
FIG._1

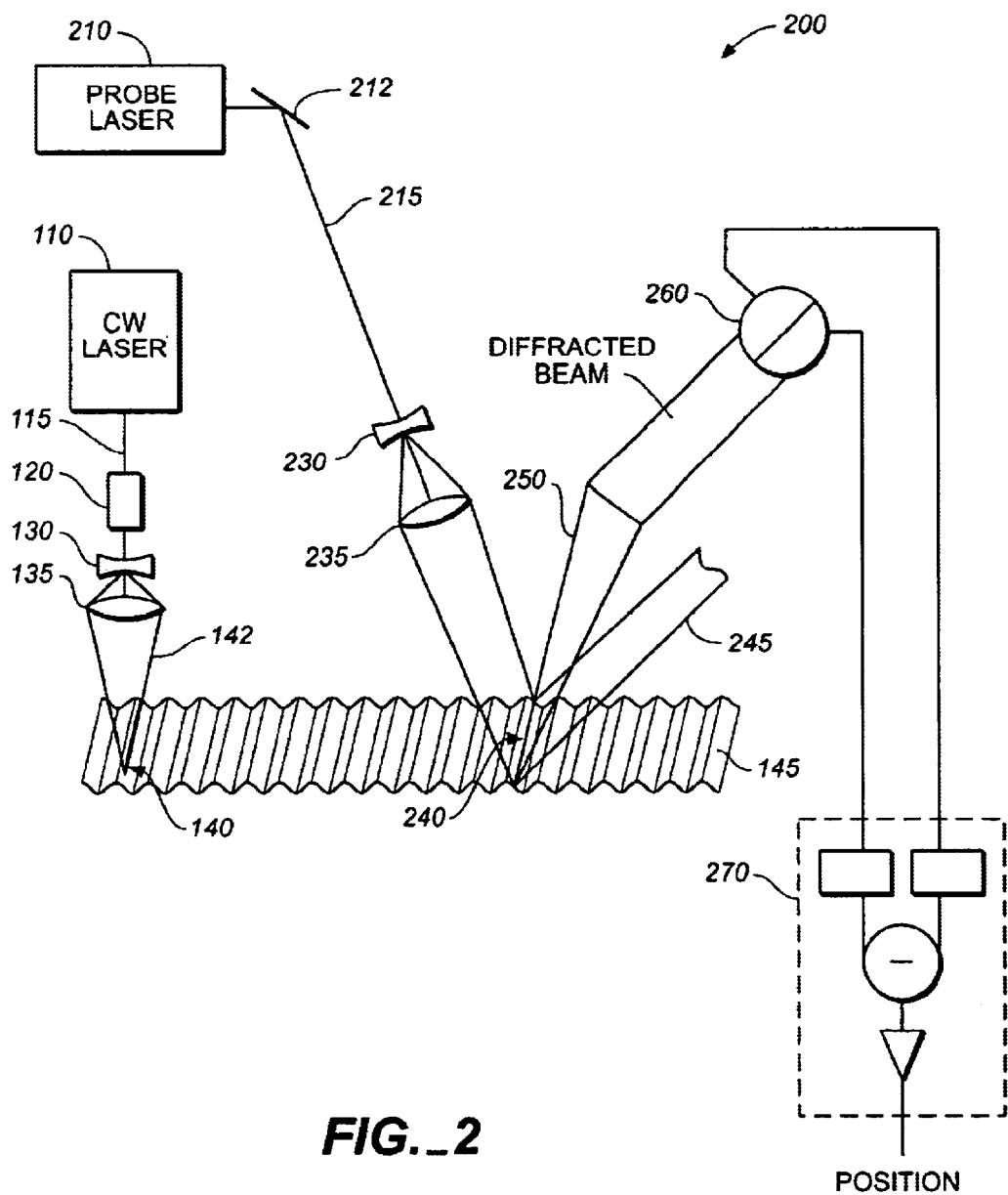
FIG._2

SURFACE PHOTO-ACOUSTIC FILM MEASUREMENT DEVICE AND TECHNIQUE

BACKGROUND

1. Field of the Invention

This invention generally relates to nondestructive evaluation of a material, and more specifically to surface photo acoustic wave measurement to determine thickness or other properties of a material used in semiconductor device fabrication.

2. Related Art

During fabrication of microelectronic devices, thin films of metals and metal alloys are deposited on silicon wafers and used as electrical conductors, adhesion-promoting layers, and diffusion barriers. Microprocessors, for example, use metal films of copper, tungsten, and aluminum as electrical conductors and interconnects, titanium and tantalum as adhesion-promoting layers, and titanium nitride and tantalum nitride as diffusion barriers. Thickness variations in these films can modify their electrical and mechanical properties, thereby affecting the performance of the microprocessor. The target thickness values of metal films vary depending on their function: Conductors and interconnects are typically 3000–10000 angstroms thick, while adhesion-promoting and diffusion-barrier layers are typically between 100–500 angstroms thick.

Metal films are typically deposited and patterned in complex geometries in the microprocessor. A geometry currently used in microelectronics fabrication is a "damascene" or "dual damascene" structure. Damascene-type structures, used primarily to form copper conductors and interconnects, are typically formed by a multi-step process: i) an oxide layer on a wafer is first etched to have a series of trenches and then coated with a diffusion-barrier layer of tantalum or tantalum nitride; ii) copper is electrolytically plated onto the wafer to fill the coated trenches; iii) the structure is then mechanically polished to remove excess copper, leaving only trenches filled with the diffusion-barrier layer and copper. The resulting structure is a series of separated copper lines having a thickness of a few thousand angstroms, a width and periodicity of about 0.5 microns, and a length of several millimeters.

Non-metal thin films also have considerable application in low dielectric constant (k) applications such as optical coatings, sensors, and insulating films for use in ULSI circuit devices. Silica aerogel films are of particular interest. The porosity and density of the insulating film are difficult to measure but are directly related to the dielectric constant (k). Young's modulus is another important property to be measured that is also correlated with k.

During typical fabrication processes, films are deposited to have a thickness of within a few percent (e.g., 5–100 angstroms) of their target value. Because of these rigid tolerances, film thickness is often measured as a quality-control parameter during and/or after the microprocessor's fabrication. Noncontact, nondestructive measurement techniques (e.g., optical techniques) are preferred because they can measure patterned "product" samples, (e.g., damascene samples) rather than "monitor" samples. Measurement of product samples accurately indicates errors in fabrication processes and additionally reduces costs associated with monitor samples.

One optical technique for film-thickness measurements uses a single, short (100 fs) optical pulse to generate an acoustic pulse that propagates into a multilayer structure. The acoustic pulse reflects off various interfaces (i.e., layer/layer and substrate/layer interfaces) in the structure, thus causing its echo to return to the structure's surface. The returning echo pulse modulates the surface reflectivity and is measured with a variably delayed optical probe pulse. The thickness of the layers in the structure is determined by analyzing the time dependence of the reflected probe beam and the sound velocities of the film and substrate materials.

In another prior technique, a measurement system launches a surface acoustic wave with known wavelength $\lambda$. A fixed wavelength is imprinted on the wave by illuminating the copper surface with a powerful pulsed laser. The laser beam is divided into multiple beams so that an array of alternating light regions (constructive interference) and dark regions (destructive interference) as above. The period of the array is the imprinted wavelength. The copper is heated and expands in the region of the light stripes, and surface acoustic waves are launched in the two opposite directions perpendicular to the stripes. The surface acoustic wave is a series of ripples on the surface and effectively forms a diffraction grating. A second laser beam is diffracted off the grating and the surface acoustic wave frequency is imprinted on this second beam. The wave frequency is measured by the time dependence of the diffracted beam intensity. If the frequency is measured by the system, then the wave speed c can be calculated. Once c is known, the film thickness can be determined if the material acoustic constants are known.

SUMMARY OF THE INVENTION

A first aspect of the invention is a method for determining the thickness, density or other properties of a material that involves producing an acoustic wave at a first frequency in a material layer with a first laser beam. After the wave with a known frequency is created within the material layer, the angle of diffraction of a second laser beam from the acoustic wave is measured. With the measured angle of diffraction and the known frequency of the wave, the wavelength of the acoustic wave and thickness of the material layer or layers are then determined.

Another aspect of the invention is a system for measuring the thickness, density or other properties of a material. The system comprises a first laser, the first laser creating a first beam, the first beam creating an acoustic wave at a first frequency in the material, a second laser, the second laser creating a second beam, a portion of which is reflected and a portion of which is diffracted by the material, and a position sensing detector that measures the angle of diffraction of the diffracted portion of the second beam.

BRIEF DESCRIPTION OF THE FIGURES

FIG. 1 is a schematic of a first embodiment of the invention.

FIG. 2 is a schematic of a second embodiment of the invention.

DETAILED DESCRIPTION OF THE INVENTION

The fundamental physical basis of surface acoustic wave measurement is that the phase velocity, or sinusoidal wave speed, depends in part on the thickness of the layer in which it propagates. The wave speed also depends on the acoustic constants of both the film and the substrate, as well as the wavelength or frequency of the wave. The speed, wavelength, and frequency for any wave are connected by the following relation:

$$c = v\lambda_l$$

where c is the phase velocity, v is the frequency and λ is the wavelength. For a given film material, substrate material, and film thickness, c is fixed but will be unknown because the film thickness is unknown.

Referring to FIG. 1, optical system 100 creates an acoustic wave 145 with a definite frequency and measures the wavelength of the acoustic wave 145.

Continuous wave (CW) excitation laser 110 creates an excitation beam 115. The wavelength of CW laser 110 and beam 115 is selected based upon the material to be tested, and will be different for different applications. For instance, to measure a roughly one micron copper layer, a green, frequency doubled YAG or UV laser is preferred. CW laser 110 can be modulated at any frequency ranging from 100 MHz to 2 GHz. Although laser 110 is illustrated as a CW laser, a pulsed laser or any laser that can excite a wave with a known frequency may be used in place of a CW laser. Preferably, if employed, the pulsed laser should have a pulse length of roughly 1 microsecond or longer. Beam 115 travels through acousto-optic modulator 120, which modulates the beam at a definite frequency, p, of, for instance, 300 MHz. The focused beam 142 is in the form of a single narrow stripe, not an array, with no wavelength or q associated with it. Beam 115 passes through and is focused by cylinder lens combination 130 and 135 in the form of a narrow stripe and repetitively heats a small rectangular region 140 of copper at the same frequency (300 MHz) and the resulting expansion launches surface acoustic waves 145 in opposite directions perpendicular to the rectangular region 140. The illuminated rectangular region 140 is about 1 micron by about 50–100 microns. These waves 145 have a wavelength $\lambda_a$ and form a diffraction grating.

The wavelength $\lambda_a$ of the acoustic waves 145 is determined by diffracting a probe laser beam 215 from the grating and measuring its angle of diffraction θ. Any order of diffraction can be measured, however, it is preferable to measure the first order to maximize the signal to noise ratio. The angle of diffraction is used to calculate the wavelength of the acoustic wave according to the following formula:

$$\lambda_l = 2\lambda_a \sin \theta$$

where $\lambda_l$ is the wavelength of the laser light in probe beam 215, $\lambda_a$ is the wavelength of the acoustic wave, and θ is the diffraction angle. The wavelength of the laser light $\lambda_l$ is known or can be measured or determined by any number of ways well known in the art.

With the calculated acoustic wavelength $\lambda_a$, and the known frequency of the acoustic wave 145, which is the same as the modulation frequency of laser light that induced the wave (300 MHz), the speed of the wave can be calculated with the formula $$c = v\lambda_a$$

Once c is known, the film thickness can be determined after the material acoustic constants of the material are measured. The material acoustic constants are: the transverse and longitudinal speeds of sound in the substrate material, the transverse and longitudinal speeds of sound in the film material, and the densities of the substrate and film materials. The thickness can be calculated from the measured acoustic wave speed c; the imposed frequency v (300 MHz), and the material constants using acoustic dispersion relations. Acoustic dispersion relations are theoretically calculated data and/or data plots for different layer/substrate combinations relating frequency to velocity or other characteristics. The thickness can then be determined by referencing in real-time the dispersion curves which can be stored in a memory of optical system 100.

For further explanation of the dispersion relations please refer to "Real-time optical characterization of surface acoustic modes of polyimide thin-film coatings", Anil R. Duggal, John A. Rogers, and Keith A. Nelson, Journal of Applied Physics, 72, (1992), pp.2823–2839, which is hereby incorporated by this reference in its entirety.

The density and Young's modulus of low-k dielectric films on a substrate can also be determined by exciting a surface acoustic wave within the substrate. This is possible because these films, unlike copper or other metal films, are transparent. The transparency will prevent them from absorbing much laser light, which will then be absorbed by an underlying copper or silicon substrate. The substrate will absorb some of the laser light and create the acoustic wave. If data is taken at more than one frequency, the acoustic dispersion curve can be mapped out and the density as well as the acoustic wave speed within the substrate and films on the substrate can be determined. Four properties of a layer affect the dispersion curve shape, the thickness, density, Young's Modulus, and Poisson's ratio. One or more of these variables can be fitted to the dispersion curve, and from the best fit, the desired layer property can be determined. The density is closely related and can be used to determine film properties such as the dielectric constant, stiffness (Young's modulus), thermal conductivity, and pore size by referencing the previously gathered acoustic dispersion curves. The density can also be used to calculate Young's modulus, (a measure of the strength of the film material) as density varies with the following relation:

$$E = E_0 (\rho/\rho_0)^m$$

where E is Young's modulus, $E_0$ is the modulus at an initial density, ρ is the density, $\rho_0$ is the initial density, and m is a constant with value of about 3–4. Young's modulus is also directly related to the dielectric constant of the material which can be determined by referencing experimental data correlating Young's modulus with the dielectric constant.

For further explanation please refer to "Characterization of thin-film aerogel porosity and stiffness with laser-generated surface acoustic waves", C. M. Flannery, C. Murray, I. Streiter, S. E. Schulz, Thin Solid Films, 388, (2001), pp. 1–4, which is hereby incorporated by this reference it its entirety.

Referring again to FIG. 1, beam 215 produced by probe laser 210 is reflected by mirror 212, and modulated by modulator 220 at a frequency that differs from the beam 115 by about 100 Hz to 100 kHz. Probe laser 210 can be a CW laser or a pulsed laser as described above regarding laser 110. In this example, a frequency difference of 1 kHz is illustrated between beam 115 and 215. Therefore beam 215 is modulated at 300.001 MHz before being focused onto the material by lenses 230 and 235. A CW pump laser 110 with a large, but reasonable, power of 10 W will produce surface ripples about 0.2 Å high. These small ripples diffract only a small fraction, around $10^{-7}$, of the probe laser light. With a visible or near-IR probe laser power of 100 mW, there is about 10 nW or $10^{10}$ photons/sec in the diffracted beam 250. This power is adequate for a precision measurement. With an incident angle of 45° the first order diffracted beam 250 is 10° away from the specularly reflected beam 245. With a measurement spot 240 of 100 μm length, there are about 20 ripples within the spot and this would make the diffracted beam width about 0.5 degree (the size of the ripples has been exaggerated in the figures for illustrative purposes). In order to make a measurement of film thickness with about 0.5% accuracy, the diffraction angle θ must be measured to about 1%, or 0.1 degree. This involves finding the center of the diffracted spot within about ⅕th of its width. This is possible with about $10^{10}$ photons. Thus, at a position sensing detector 260 located 150 mm away from the surface of the metal, 0.1 degrees corresponds to 250 microns.

Position sensing detector 260 is shown as a split detector, although any type of position sensing detector, a component well known in the art, can be employed. A split detector is two or more detectors spaced very closely, often arranged as sectors of a circular disk. By combining the separate photocurrents from the detector in various ways, such as subtracting them or computing their ratio, small changes in the beam position can be measured very accurately. One problem with split detectors is that a portion of the light that falls between the two cells is lost. Lateral-effect cells are another type of position sensing device that avoids the problem of split detectors. They are single large photodiodes that use a thin, highly resistive layer for the top electrode of the cell, each end of which has its own lead. The output leads are connected to low-impedance points. The light beam appears as a current source located somewhere on the surface, so that the photocurrent divides itself between the output pins in proportion to the conductance of each path. Because the conductance depends on the distance from the light beam to the output pin, the ratio of the currents in each pin gives the location of the light source. The position sensing detector 260 could also be discrete diodes with a shadow mask or any type of position sensing detector used in the art.

Lock-in detector/amplifier 270 detects or amplifies only the difference frequency (between excitation laser 110 and probe laser 210) at 1 kHz. Optical system 100 has sufficient signal-to-noise ratio and resolution so that an accurate measurement within 0.5% can be made. A microprocessor (not shown) may also be integrated into the circuitry of optical system 100.

There is at least one major difficulty in measuring the angle of diffraction of the surface wave that is overcome by optical system 100. The small amplitude surface ripples (about 0.2 Å) may be approximately as much as a factor of 100 smaller than the inherent surface roughness. This means that the probe beam 215 will be scattered over a wide range of angles, including those of the diffracted beam 250, with a total intensity about $10^4$ times larger than the diffracted beam. Looking for this needle in a haystack might seem impossible, except for the fact that the diffracted light has the frequency of the acoustic ripples imprinted on it (300 MHz), and the scattered light does not. One way to use this fact is to modulate the probe beam 215 at a slightly different frequency, for instance, 300.001 MHz. The probe beam 215 can be modulated at any frequency, but preferably at a frequency such that the difference (from the excitation or pump beam) is about 100 Hz to 100 kHz. In the example above where the difference frequency is 1 kHz, the diffracted probe light would then have several frequency components, including the difference frequency of 1 kHz. The position sensitive detector 260 is used with lock-in amplification/detection set at 1 kHz to monitor only the diffracted beam and reject the stray scattered light. This scheme also would reject the scattered light from the excitation laser beam 115.

FIG. 2 illustrates optical system 200, another embodiment of the invention. Optical system 200 differs from optical system 100 of FIG. 1 in that it lacks the acousto-optic modulator 220. Also, position sensing electronics 270 measure the frequency over a range of frequencies, not just a particular frequency (1 kHz for example) as in optical system 100. Optical system 200 is thus simpler than optical system 100 but also less accurate because the stray scattered light would not be rejected as described above with regard to optical system 100.

The system and method of the present invention are advantageous over prior techniques. Although any laser that can create an acoustic wave of known frequency is within the scope of this invention (e.g. pulsed), the preferred CW laser measurement techniques described have better signal-to-noise than pulsed laser techniques, due to the much greater stability of CW lasers. In addition, measuring the difference frequency between the laser beams rejects any inaccuracy from the scattered light resulting in a more accurate and reliable measurement and system.

While particular embodiments of the present invention and their advantages have been shown and described, it should be understood that various changes, substitutions, and alterations can be made therein without departing from the spirit and scope of the invention as defined by the appended Claims. For example, different frequencies of modulation can be used and multiple measurements at more than one frequency, even for the same material and thickness can be performed. These multiple measurement frequencies can be used to determine the film thickness, acoustic constants, density, porosity, stiffness, and Poisson's ratio of the bulk material or of layers upon the bulk material. Furthermore, different types and configurations of the lenses, and position detectors are also within the scope of the invention. Those skilled in the art will realize that other types of lasers and different frequency modulations are within the scope of the invention.

What is claimed:

1. A method for determining the thickness of a layer on a semiconductor comprising:

producing a surface acoustic wave at a first frequency in the layer with a first laser beam;

measuring the angle of diffraction of a second laser beam from the surface acoustic wave; and calculating the wavelength of the surface acoustic wave and thickness of the layer from the angle of diffraction.

2. The method of claim 1 wherein producing the surface acoustic wave at the first frequency comprises modulating the intensity of the first laser beam and focusing the modulated first laser beam on the surface of the layer.

3. The method of claim 2, further comprising modulating the intensity of the second laser beam at a second frequency prior to the measuring of the angle of diffraction.

4. The method of claim 3, wherein measuring of the angle of diffraction further comprises amplifying a third frequency equal to a difference between the first and second frequencies.

5. the method of claim 4, wherein the third frequency is about 100 Hz to 100 KHz.

6. The method of claim 2, wherein the first frequency is within the range of about 100 MHz to 2 GHz.

7. The method of claim 6, wherein the first frequency is about 300 MHz.

8. The method of claim 1, wherein the angle of diffraction is measured by a position sensitive detector.

9. The method of claim 1, wherein the surface acoustic wave is produced by a modulated continuous wave laser beam.

10. The method of claim 1, wherein the measuring measures the angle of diffraction of a first or higher order diffraction of the second laser beam.

11. A system for measuring a property of a material comprising:

a first laser, the first laser creating a first beam, the first beam creating an surface acoustic wave at a first frequency in the material;

a second laser, the second laser creating a second beam, a portion of which is diffracted by the surface acoustic wave in the material; and a position sensing detector that measures the angle of diffraction of the diffracted portion of the second beam.

12. The system of claim 11, further comprising a modulator that is different from the material and that modulates the intensity of the first beam at the first frequency.

13. The system of claim 12, further comprising a modulator that is different from the material and that modulates the intensity of the second beam at a second frequency.

14. The system of claim 13 wherein the second frequency differs from the first frequency by about 100 Hz to 100 kHz.

15. The system of claim 13, further comprising circuitry that amplifies a signal from the position sensing detector at a third frequency equal to the difference of the first and the second frequencies.

16. The system of claim 12, wherein the first frequency is about 100 MHz to 2 GHz.

17. The system of 16, wherein the first frequency is about 300 MHz.

18. The system of claim 11, further comprising circuitry that calculates a property of the material from the angle of diffraction.

19. The system of claim 18 wherein the property calculated is the thickness of the material.

20. The system of claim 18 wherein the property calculated is the density of the material.

21. The system of claim 18 wherein the property calculated is the modulus of elasticity of the material.

22. The system of claim 18 wherein the property calculated is the dielectric constant of the material.

23. The system of claim 18, wherein the circuitry comprises a microprocessor.

24. The system of claim 11, wherein the first laser beam comprises a modulated continuous wave laser beam.

25. The system of claim 11, wherein the detector measures the angle of diffraction of a first or higher order diffraction of the second laser beam.

26. A method for determining a property of substrate or layer upon a substrate comprising:

heating a region of the substrate with a first laser beam modulated at a first constant frequency so as to launch surface acoustic waves at the first frequency within the substrate and layer upon the substrate; and measuring the angle of diffraction of a second laser beam from the surface and/or the substrate.

27. The method of claim 26, further comprising:

calculating the wavelength of the surface acoustic waves from the angle of diffraction;

calculating the speed of the surface acoustic waves from the frequency and wavelength of the surface acoustic waves; and calculating a property of the substrate and layer upon the substrate from the speed of the surface acoustic wave.

28. The system of claim 27, wherein the property calculated is the thickness of the material.

29. The system of claim 27 wherein the property calculated is the density of the material.

30. The system of claim 27 wherein the property calculated is the modulus of elasticity of the material.

31. The system of claim 27 wherein the property calculated is the dielectric constant of the material.

32. The method of claim 26, wherein the range of the first frequency is about 100 MHz to 2 Hz.

33. The method of claim 32, wherein the first frequency is about 300 MHz.

34. The method of claim 26, further comprising modulating the frequency of the second laser beam at a second constant frequency prior to the measuring of the angle of diffraction.

35. The method of claim 34, wherein the second frequency is modulated so that it differs from the first frequency by about 100 Hz to 100 kHz.

36. The method of claim 34, wherein a frequency component of the diffracted second beam equal to the difference of the frequency of the first and second beams is used to determine the angle of diffraction of the diffracted beam.

37. The method of claim 26, wherein when measuring the angle of diffraction the second laser beam is diffracted to a position sensing detector.

38. The method of claim 37, wherein the position sensing detector measures the angle of diffraction of the diffracted beam, and the angle of diffraction is used to determine the wavelength of the surface acoustic wave.

39. The method of claim 26, wherein the region is heated by the first laser beam comprising a modulated continuous wave laser beam.

40. The method of claim 26, wherein the measuring measures the angle of diffraction of a first or higher order diffraction of the second laser beam.

* * * * *